US011865071B2

(12) United States Patent
McDowell et al.

(10) Patent No.: US 11,865,071 B2
(45) Date of Patent: Jan. 9, 2024

(54) SYSTEM AND METHOD FOR STORING PHARMACEUTICALS OR BIOLOGICAL MEDIA

(71) Applicant: SAINT-GOBAIN PERFORMANCE PLASTICS CORPORATION, Solon, OH (US)

(72) Inventors: John G. McDowell, Delano, MN (US); Timothy A. Jenks, Plymouth, MN (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 722 days.

(21) Appl. No.: 16/541,464

(22) Filed: Aug. 15, 2019

(65) Prior Publication Data

US 2020/0054523 A1   Feb. 20, 2020

Related U.S. Application Data

(60) Provisional application No. 62/719,216, filed on Aug. 17, 2018.

(51) Int. Cl.
*A61J 1/10* (2006.01)
*A61J 1/14* (2023.01)
(Continued)

(52) U.S. Cl.
CPC ............ *A61J 1/10* (2013.01); *A61J 1/145* (2015.05); *A61J 1/1443* (2013.01); *A61J 1/1456* (2015.05);
(Continued)

(58) Field of Classification Search
CPC .. A61J 1/10; A61J 1/1443; A61J 1/145; A61J 1/1456; A61J 1/1462; A61J 1/1475;
(Continued)

(56) References Cited

U.S. PATENT DOCUMENTS 3,998,255 A * 12/1976 Mather ................... A61F 5/441
383/102
4,312,352 A * 1/1982 Meisch ..................... A61F 5/44
604/322

(Continued)

FOREIGN PATENT DOCUMENTS

CN        1155413 C       6/2004
CN      201192485 Y       2/2009
(Continued)

OTHER PUBLICATIONS

Cambridge Dictionary: above; published Dec. 15, 2016; accessed Mar. 11, 2023. (Year: 2016).*
(Continued)

*Primary Examiner* — Ariana Zimbouski
(74) *Attorney, Agent, or Firm* — Abel Schillinger, LLP; Chi Suk Kim

(57) ABSTRACT

A system for storing pharmaceuticals or biological media comprising a bag including a flexible sidewall defining an opening; and a vent coupled with the flexible sidewall at the opening and defining a vent passageway between an internal volume of the bag and an external environment, wherein the vent is coupled with the bag at a location spaced apart from and above the opening.

16 Claims, 3 Drawing Sheets

(51) Int. Cl.
  *B65D 33/01* (2006.01)
  *A61M 5/165* (2006.01)
(52) U.S. Cl.
  CPC .......... *A61J 1/1462* (2013.01); *A61J 1/1475* (2013.01); *A61J 1/1487* (2015.05); *A61M 5/165* (2013.01); *B65D 33/01* (2013.01); *A61J 1/1481* (2015.05)
(58) Field of Classification Search
  CPC ...... A61J 1/1487; A61J 1/1481; A61M 5/165; B65D 33/01; B65D 51/1616; A61F 5/441
  See application file for complete search history.

(56) References Cited

U.S. PATENT DOCUMENTS

| | | | |
|---|---|---|---|
| 4,457,758 A * | 7/1984 | Norton | A61F 5/441 55/482 |
| 4,479,818 A * | 10/1984 | Briggs | A61F 5/441 55/385.4 |
| 4,512,771 A | 4/1985 | Norton | |
| 4,863,447 A | 9/1989 | Smith | |
| 4,946,795 A | 8/1990 | Gibbons et al. | |
| 4,972,865 A | 11/1990 | Mattson | |
| 5,061,236 A | 10/1991 | Sutherland et al. | |
| 5,725,645 A | 3/1998 | Wickland et al. | |
| 5,779,902 A | 7/1998 | Zuk, Jr. | |
| 5,792,133 A | 8/1998 | Rochat | |
| 5,893,461 A | 4/1999 | Walters | |
| 6,171,493 B1 | 1/2001 | Zia et al. | |
| 6,837,268 B2 | 1/2005 | Skeens et al. | |
| 7,713,320 B2 | 5/2010 | Pham | |
| 9,335,000 B2 | 5/2016 | Selker et al. | |
| 9,376,655 B2 | 6/2016 | Larsen et al. | |
| 9,511,908 B2 | 12/2016 | Bons et al. | |
| 2004/0238397 A1 | 12/2004 | Yu et al. | |
| 2009/0126515 A1 | 5/2009 | Goodwin | |
| 2014/0366486 A1 | 12/2014 | Hinz et al. | |
| 2015/0122846 A1 | 5/2015 | Stanley et al. | |
| 2015/0129725 A1 * | 5/2015 | Zedan | H02G 3/32 248/67.5 |
| 2017/0112559 A1 | 4/2017 | Sylliaasen et al. | |
| 2021/0222103 A1 * | 7/2021 | Martin | C12M 23/14 |

FOREIGN PATENT DOCUMENTS

| | | |
|---|---|---|
| CN | 201423044 Y | 3/2010 |
| CN | 107847845 A | 3/2018 |
| JP | 06335516 A | 12/1994 |
| JP | 2008142473 A | 6/2008 |
| WO | 2004047714 A1 | 6/2004 |
| WO | 2020037104 A1 | 2/2020 |

OTHER PUBLICATIONS

International Search Report and Written Opinion for PCT/US2019/046621, dated Dec. 2, 2019, 11 pages.

* cited by examiner

SYSTEM AND METHOD FOR STORING PHARMACEUTICALS OR BIOLOGICAL MEDIA

CROSS-REFERENCE TO RELATED APPLICATION(S)

This application claims priority under 35 U.S.C. § 119(e) to U.S. Patent Application No. 62/719,216 entitled "SYSTEM AND METHOD FOR STORING PHARMACEUTICALS OR BIOLOGICAL MEDIA," by John G. MCDOWELL et al., filed Aug. 17, 2018, which is assigned to the current assignee hereof and incorporated herein by reference in its entirety.

FIELD OF THE DISCLOSURE

The present disclosure relates to systems and methods for storing pharmaceuticals or biological media.

RELATED ART

Many pharmaceutical and bioprocessing processes utilize storage containers for storing fluid associated with the pharmaceutical or biological media. In certain instances, the container can include a bag having at least one flexible portion—such as a flexible sidewall.

Many pharmaceutical and biological media containers require venting. In certain instances, venting can prevent buildup of internal pressure, release of unwanted chemicals and byproducts, enhanced air circulation, or a combination thereof.

The pharmaceutical and bioprocessing industries continue to demand better containers and associated technologies to permit more efficient storage and operation of pharmaceutical and biological containing fluids.

BRIEF DESCRIPTION OF THE DRAWINGS

Embodiments are illustrated by way of example and are not intended to be limited in the accompanying figures.

DETAILED DESCRIPTION

Figure 1:
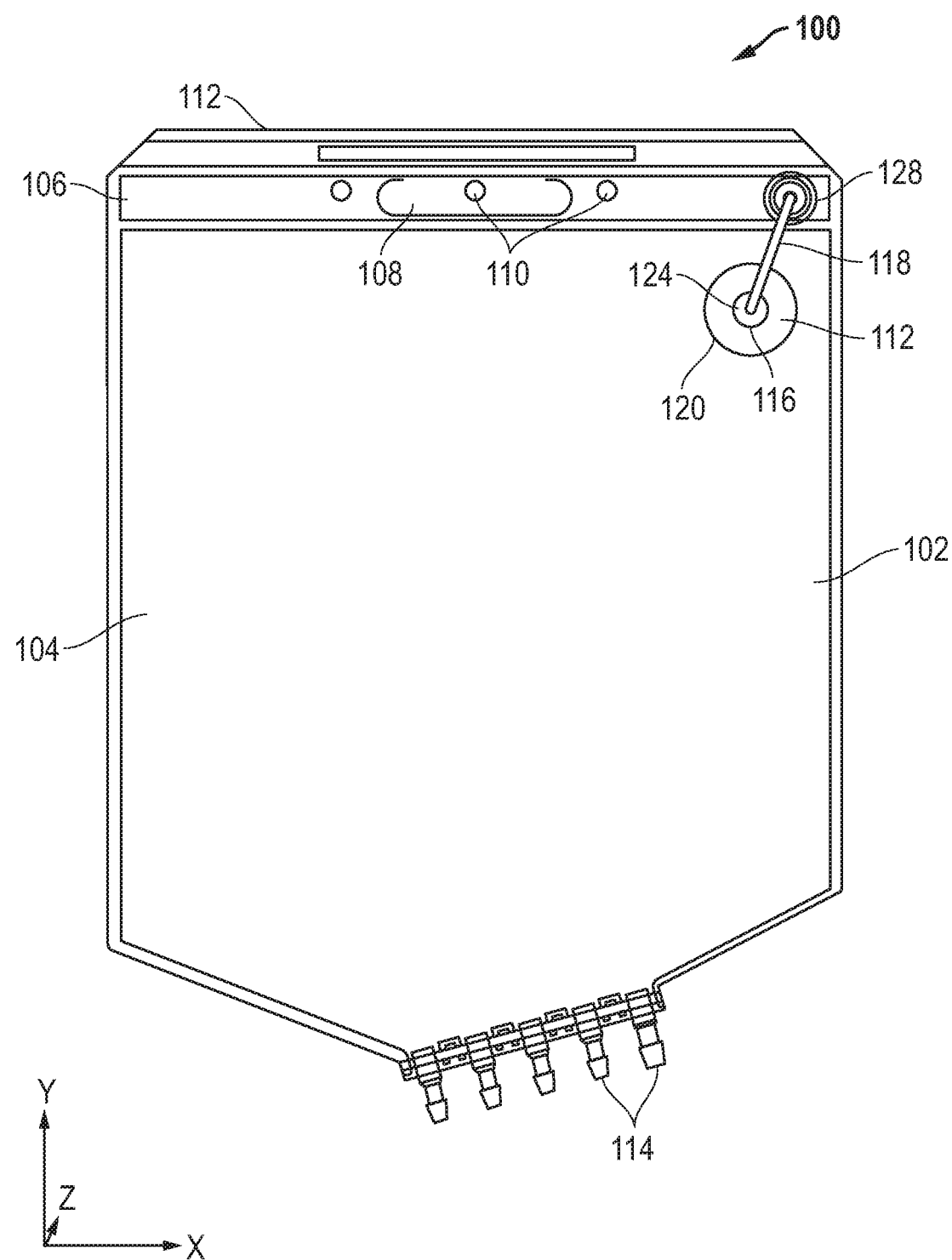
FIG. 1 includes a side view of a system in accordance with an embodiment.

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings. However, other embodiments can be used based on the teachings as disclosed in this application.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in textbooks and other sources within the pharmaceutical and biological media processing arts.

In accordance with one or more of the embodiments described herein, a system for storing pharmaceuticals or biological media can generally include a bag having a flexible sidewall defining an opening. A vent can be coupled with the flexible sidewall at or adjacent to the opening and define a vent passageway between an internal volume of the bag and an external environment. In certain instances the vent can be coupled with the bag at a location spaced apart from and above the opening. In a particular embodiment, the vent can be coupled with the bag directly above the opening such that a line extending between the opening and location of coupling between the vent and bag is vertical, or generally vertical.

In a particular embodiment, the system can further include a filter coupled with the bag. More particularly, the filter can be coupled with the bag at the location spaced apart from and above the opening. In an embodiment, the filter is disposed between the bag and an end of the vent. In such a manner, the filter can act as a spacer such that the vent doesn't contact the bag at the location spaced apart from and above the opening in the flexible sidewall.

In an embodiment, a portion of the filter can be disposed on a first side of the bag and a second portion of the filter can be disposed on a second side of the bag opposite the first side. For example, in a particular embodiment, the filter can include a disk-like shape with projections emerging from opposing major surfaces of the disk-like shape. The filter can be installed relative to the bag such that at least a portion of a first projection on the first side of the disk-like shape is disposed on the first side of the bag and at least a portion of a second projection on the second side of the disk-like shape is disposed on a second side of the bag. In a particular embodiment, the first and second projections can correspond with a fluid pathway extending through the filter. Moreover, at least one of the first and second projections can include an engagement feature, such as a barb, adapted to form an interference fit with the bag, the vent, or a combination thereof.

In an embodiment, the location above and spaced apart from the opening in the flexible sidewall can correspond with a handle portion of the bag. More particularly, the location above and spaced apart from the opening can correspond with a portion of the bag having a single sidewall (e.g., not a portion of the bag defining an internal volume adapted to receive the pharmaceutical or biological media).

A lumen extending through the filter (e.g., through the first projection, the second projection, the disk-like shaped body, or a combination thereof) can be in fluid communication with the vent pathway. In a particular instance, vented fluid, including liquid or gaseous fluid, can move between the internal volume of the bag and the external environment through the vent passageway and through the lumen.

In an embodiment, the vented fluid can move through the bag (e.g., through the flexible sidewall or through the handle portion) prior to contacting the external environment. For example, in a particular embodiment, the lumen can extend through the bag. By way of example, one of the projections on the filter can extend through the bag such that a filter input is on a first side of the bag and a filter output is on a second side of the bag opposite the first side.

In an embodiment, the lumen can be adapted to lie along a generally horizontal plane when the system is in use (e.g., when the bag contains a pharmaceutical or biological media). In a more particular embodiment, the lumen can be perpendicular with a surface of the bag.

In certain instances, the filter can be coupled with the bag prior to coupling the vent to the filter. In other instances, the filter can be coupled with the vent prior to coupling the filter to the bag.

In accordance with one or more embodiments described herein, a method of making a system for storing pharmaceuticals or biological media can include coupling a vent to an opening in a flexible sidewall of a bag. The method can further include installing a filter on the bag at a vertical elevation spaced apart from and above the opening. The method can further include attaching a free end of the vent to the filter. In certain instances, installing the filter on the bag can occur prior to attaching the free end of the vent to the filter. In other instances, attaching the free end of the vent to the filter can occur prior to installing the filter on the bag.

In certain embodiments, coupling the vent to the opening is performed by welding the vent or an intermediary element to the bag, such as to the flexible sidewall of the bag.

In an embodiment, installing the filter is performed such that fluid flow through the filter occurs in a direction generally transverse to a major surface of the bag. More particularly, installation of the filter can occur such that fluid flow through the filter occurs in a direction generally transverse to the major surface of the bag when the bag is empty and supported or at least partially filled with pharmaceutical or biological media.

In an embodiment, the method can further include forming a lumen in the bag prior to installing the filter. By way of a non-limiting example, forming the lumen can include forming an opening in the bag having a diameter less than a diameter of a portion of the filter to be received in the lumen. After forming the lumen, the filter can be installed relative to the bag at the lumen. More particularly, the filter, or a portion thereof, can be inserted into the lumen. In an embodiment, the filter can form an interference fit with the lumen.

In an embodiment, the method can further include bending the vent or a portion thereof prior to attaching the free end of the vent to the filter. More particularly, the method can include bending the vent upward from the opening in the bag. In certain instances, attaching the free end of the vent to the filter can create an approximately 180 degree bend in the vent, as viewed between the opening and the filter.

In accordance with one or more embodiments, a method of making a system for storing pharmaceuticals or biological media can include moving a free end of a vent extending from a flexible sidewall of a bag to a location above a non-free end of the vent. The method can further include coupling the free end of the vent to the bag.

In an embodiment, the method can further include coupling a filter to the bag. More particularly, coupling the filter to the bag can include coupling a barb portion of the filter with a lumen in the bag. In an embodiment, coupling the filter to the bag can be performed such that the barb passes from a first side of the bag to a second side of the bag opposite the first side.

In certain instances, biasing the free end of the vent is performed such that the non-free end of the vent is disposed at a vertical elevation below the free end of the vent.

In a particular instance, systems and methods described herein can be adapted for use with pharmaceuticals and biological media. In an embodiment, the systems and methods described herein can be used to maintain integrity of the filter during operation. More specifically, embodiments described herein can prevent filter wetting which can occur when fluid stored in the bag contacts the filter. In particular, embodiments described herein can reduce or prevent capillary action of fluid within the vent passageway that might cause wetting of the filter. Such wetting can lead to damaged fluid (particularly for sensitive pharmaceuticals), a damaged filter, or a combination thereof.

FIG. 1 includes a side view of a system 100 in accordance with an embodiment. The system 100 can generally include a bag 102 having a flexible sidewall 104 coupled with a handle portion 106. In an embodiment, the flexible sidewall 104 can include two or more sheets of material coupled together. For example, by way of a non-limiting embodiment, the flexible sidewall 104 can include a first piece of material welded to a second piece of material. More particularly, the first and second pieces can be welded adjacent to the at least some of the edges thereof. In certain embodiments the bag 102 can include a collapsible bag.

In the illustrated embodiment, the handle portion 106 is disposed at a different vertical elevation as compared to the flexible sidewall 104. More particularly, the handle portion 106 is disposed at a vertical elevation above the flexible sidewall 104. In another embodiment, the handle portion 106 can be integral with the flexible sidewall 104. The handle portion 106 can include a handle 108 adapted to permit user grasp of the system 100. In certain embodiments, the handle 108 can be centered relative to the bag 102 as viewed when the bag 102 is empty and flattened on its side. In an embodiment, the handle portion 106 can include one or more engagement elements 110 adapted to permit engagement of the system 100 with an equipment (not illustrated), such as a rack, for filling, storing, transporting, or otherwise operating on fluid to be contained within the system 100.

In an embodiment, the handle portion 106 can be formed from portions of the flexible sidewall 104 extending vertically upward from the flexible sidewall 104. That is, the handle portion 106 can be integral with the flexible sidewall 104 of the bag 102—or more particularly an upper portion of the flexible sidewall 104.

In another embodiment, the handle portion 106 can be formed from a discrete component coupled to the flexible sidewall 104. In a particular embodiment, the handle portion 106 can have a material composition different than the flexible sidewall 104. In another particular embodiment, the handle portion 106 can have a material composition the same as the flexible sidewall 104.

In an embodiment, the handle portion 106 can extend from only part of the flexible sidewall 104. That is, in an embodiment, the handle portion 106 can extend around less than 100% of the circumference of the bag 102. For example, in a particular embodiment, the handle portion 106 can extend around approximately 50% of the circumference of the bag 102. In certain instances the bag 102 can be formed from two pieces of material welded together and the handle portion 106 can be formed from only one of the two pieces. In another embodiment, the handle portion 106 can extend around the entire circumference of the bag 102. In yet a further embodiment, the handle portion 106 can extend around at least 10% of the circumference of the bag 102, at least 25% of the circumference of the bag 102, at least 50% of the circumference of the bag 102, or at least 75% of the circumference of the bag 102.

In an embodiment, the bag 102 can define a main opening 112 to permit filling of an internal volume of the bag 102. The main opening 112 can be disposed, for example, along an upper section of the bag 102, such as adjacent to or within the handle portion 106. The main opening 112 can be selectively closable to selectively prevent unwanted fluid ingress or egress into and from an internal volume of the bag 102. When not in use, the main opening 112 typically remains closed to maintain sterility of the internal volume.

The system 100 can include one or more fluid ports 114 adapted to permit, for example, sampling, transport, draining, or removal of fluid from the bag 102. In a particular embodiment, at least one of the one or more fluid ports 114 can be disposed along a lower section of the bag 102, such as for example, along a lower edge of the bag 102. In an embodiment, the system 100 can include at least one fluid port 114, at least two fluid ports 114, at least three fluid ports 114, at least four fluid ports 114, or at least five fluid ports 114. In another embodiment, the system 100 can include no greater than twenty fluid ports 114, no greater than fifteen fluid ports 114, or no greater than ten fluid ports 114. In the illustrated embodiment, the fluid ports 114 have a same shape and size. In other embodiments, the fluid ports 114 can have different shapes, sizes, lumen diameters, operational capacities, or any combination thereof relative to one another. The one or more fluid ports 114 can be coupled with fluid lines adapted to permit transport of fluid from the bag 102 to an equipment or other fluid destination.

In an embodiment, the bag 102 can include an opening 116 in the flexible sidewall 104. The opening 116 can extend through the flexible sidewall 104 and be in fluid communication with the internal volume of the bag 102.

In an embodiment, the opening 116 is disposed above a fill-line of the bag. As used herein, the "fill-line" can refer to a prescribed capacity, or a maximum operational capacity, of the bag 102 as defined by the height of the internal volume. Elements disposed above the fill-line can stay dry while elements below the fill-line can contact the fluid. While the fill-line can refer to a maximum fill-line of the bag, the fill-line can also be relative to the volume of fluid within the bag 102. Thus, in an embodiment, the fill-line can correspond with the relative fluid level in the bag 102 at any given moment. Elements above the relative fill-line remain dry while elements below the relative fill line come into contact with the fluid.

A vent 118 can be coupled with the flexible sidewall 104 of the bag 102. In an embodiment, the vent 118 can be coupled with the flexible sidewall 104 at or adjacent to the opening 116. In an embodiment, the vent 118 can be coupled to the flexible sidewall 104 through an intermediate element 120. The intermediate element 120 can include a flanged portion 122 adapted to couple with the flexible sidewall 104 and a passageway 124 extending from the flanged portion 122. In an embodiment, the intermediate element 120 can be permanently coupled with the flexible sidewall, such as welded to the flexible sidewall 104. More particularly, in an embodiment, the flanged portion 122 of the intermediate element 120 can be ultrasonically welded to the flexible sidewall 104. In certain instances, the flanged portion 122 can be removably coupled to the flexible sidewall 104.

The vent 118 can include a tube defining a vent passageway (not illustrated). The vent passageway can extend between the internal volume of the bag 102 and the external environment. In an embodiment the vent 118 can be formed from or include a flexible material.

In an embodiment, the vent passageway can be in fluid communication with the passageway 124 of the intermediate element 120. In a particular instance, the vent 118 can be engaged with the passageway 124 via an interference fit. In another particular instance, the vent 118 can be welded to the passageway 124. In yet a further embodiment, the vent 118 can be coupled with the flanged portion 122 of the intermediate element 120. By way of example, the vent 118 can be welded, adhered, or mechanically secured to the intermediate element 120. One or more mechanical features, such as clamps (not illustrated), bands, ratchets, or other readily known securing devices can be used to secure the vent 118 to the intermediate element 120.

Figure 2:
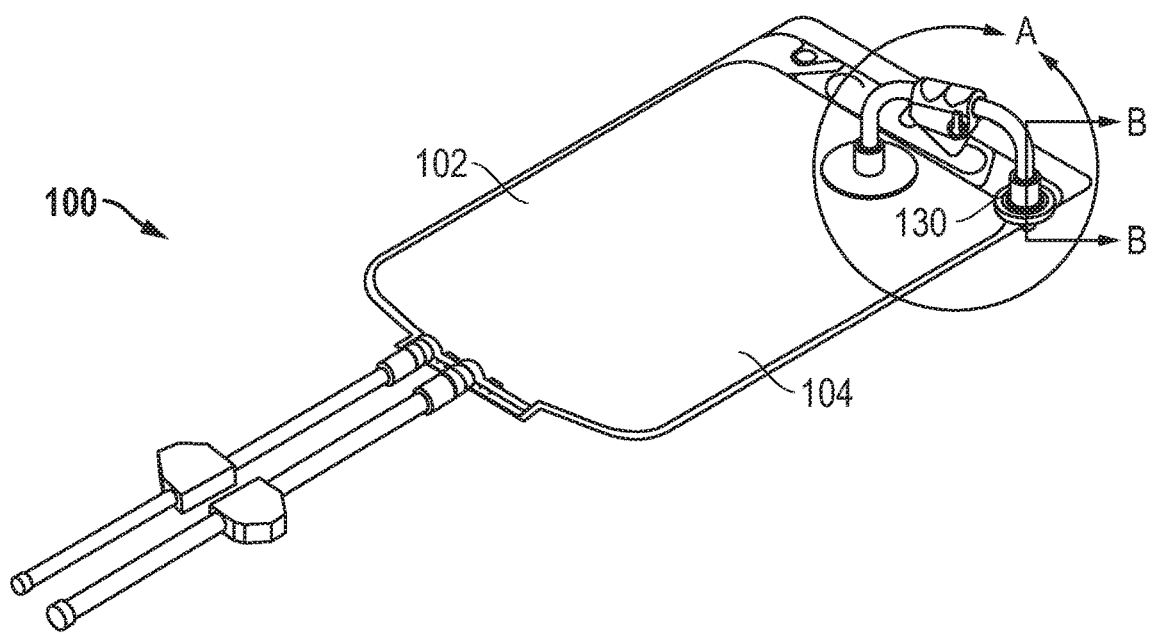
FIG. 2 includes a perspective view of a system in accordance with an embodiment in an empty state.
Figure 3:
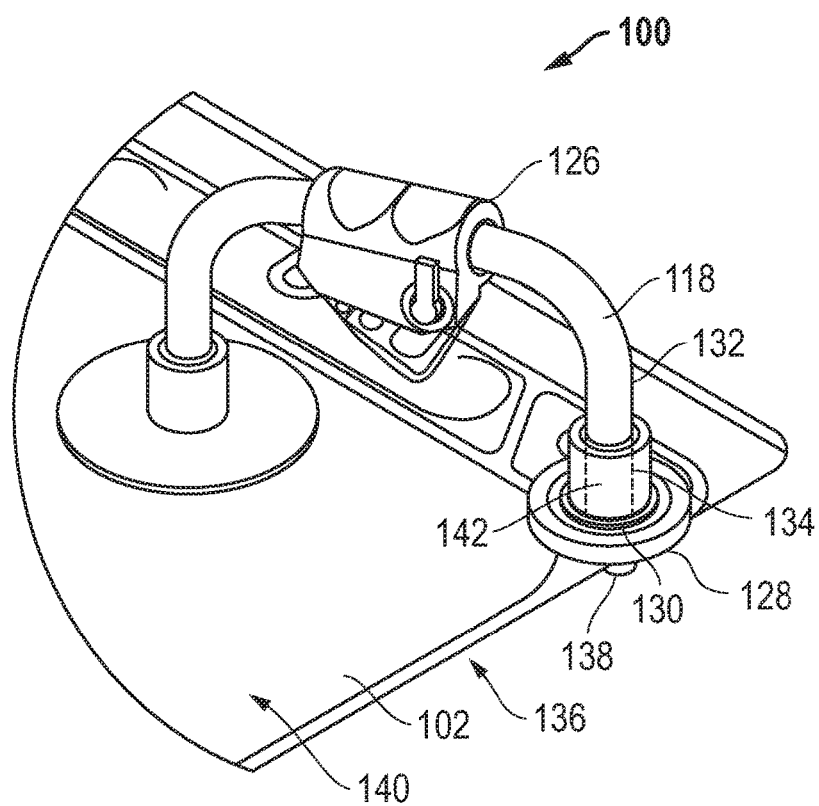
FIG. 3 includes an enlarged view of a portion of the system in accordance with an embodiment, as viewed in Circle A in FIG. 2.

Referring to FIGS. 2 and 3, in an embodiment, the vent 118 can include a fluid restrictor 126 adapted to permit selective restriction of fluid flow through the vent passageway. In an embodiment, the fluid restrictor 126 can include a hose clamp, a valve, a toggle, another fluid restricting device, or a combination thereof. In a certain instance, the fluid restrictor 126 can be manually operated, such as by hand. In another instance, the fluid restrictor 126 can be operated by a logic device, such as a microprocessor. As illustrated, and in accordance with certain embodiments, the fluid restrictor 126 can be disposed at a central, or generally central, location along the vent 118. In an embodiment, fluid flow through at least a portion of the fluid restrictor 126 can occur along a plane generally tangent with the flexible sidewall 104 at the location of the fluid restrictor 126 when the bag 102 contains fluid. Alternatively, fluid flow through at least a portion of the fluid restrictor 126 can occur along a plane generally tangent with the flexible sidewall 104 at the location of the fluid restrictor 126 when the bag 102 is empty and flattened on its side. As used herein, "empty and flattened on its side" can refer to the orientation generally illustrated in FIGS. 2 and 3, where the bag 102 lies flat.

In certain instances, the vent passageway can lie along a line having a generally curved profile. In a particular embodiment, the vent passageway can lie along, or generally along, an arc forming an approximately 180 degree bend in the vent 118.

In an embodiment, the vent 118 can be coupled with the bag 102 at a location 128 spaced apart from and above the opening 116. In a particular embodiment, the location 128 can be directly above the opening 116. Thus, for example, a line intersecting the opening 116 and the location 128 can be disposed along a Y-axis (vertical) when the bag 102 is upright (FIG. 1).

In another embodiment, the location 128 can be laterally offset from the opening 116. In such a manner, a line between the location 128 and the opening 116 can have an X-component and a Y-component. In certain embodiments, the X-component of the line can be greater than the Y-component of the line. For example, the X-component can be at least 1.01 times greater than the Y-component, at least 1.05 times greater than the Y-component, at least 1.1 times greater than the Y-component, at least 1.25 times greater than the Y-component, or at least 1.75 times greater than the Y-component. In other embodiments, the Y-component of the line can be greater than the X-component of the line. For example, the Y-component can be at least 1.01 times greater than the X-component, at least 1.05 times greater than the X-component, at least 1.1 times greater than the X-component, at least 1.25 times greater than the X-component, or at least 1.75 times greater than the X-component.

In an embodiment, the Y-component of the line, as measured between the opening 116 and the location 128, can be at least 5 mm, at last 10 mm, at least 50 mm, at least 100 mm, or at least 250 mm. In another embodiment, the Y-component of the line, as measured between the opening 116 and the location 128, can be no greater than 2000 mm, no greater than 1000 mm, no greater than 500 mm, or no greater than 300 mm.

In an embodiment, the line between the opening 116 and location 128 an be angularly offset from a Y-axis by at least 1°, at least 2°, at least 3°, at least 4°, at least 5°, at least 10°, at least 20°, at least 30°, at least 40°, at least 50°, or at least 60°. In another embodiment, the line can be angularly offset from the Y-axis by no greater than 90°, no greater than 85°, no greater than 80°, no greater than 75°, no greater than 70°, or no greater than 65°.

In an embodiment, the location 128 is disposed adjacent to the handle portion 106 of the bag 102. In a more particular embodiment, the location 128 is disposed adjacent to the handle 108. In an embodiment, the location 128 is disposed within the handle portion 106 of the bag 102. Thus, for example, the vent 118 can extend between locations along the flexible sidewall 104 and the handle portion 106.

In certain instances, the location 128 is adapted to be disposed above the fill-line of the bag 102. More particularly, the location 128 can be disposed above the fill-line of the bag 102, as measured when the bag 102 is full of fluid. In certain instances, the opening 116 can be disposed above the fill-line.

Referring to FIG. 3, the system 100 can include a filter 130 coupled with the bag 102. In a more particular embodiment, the filter 130 can be coupled with the bag 102 at or adjacent to the location 128.

In an embodiment, the filter 130 can extend through the bag 102 at the location 128. In a more particular embodiment, the filter 130 can define a lumen 142 extending through the bag 102. In yet a more particular embodiment, the lumen 142 can define a central axis extending perpendicular, or generally perpendicular with a major surface 144 of the bag 102 when the bag is empty and flattened on its side.

The filter 130 can be coupled with the vent 118. In an embodiment, the filter 130 can be disposed at an end 132 of the vent 118. The end 132 of the vent 118 can be opposite the end coupled with the bag 102 at or adjacent to the opening 116.

In certain instances, the filter 130 can be disposed between the bag 102 and the end 132 of the vent 118. That is, for example, the end 132 of the vent 118 can be spaced apart from the bag 102 by the filter 130.

In the illustrated embodiment, a first portion 134 of the filter 130 is disposed on a first side 136 of the bag 102 and a second portion 138 of the filter 130 is disposed on a second side 140 of the bag 102. In a particular embodiment, the first side 136 and second side 140 of the bag 102 can be opposite sides of the bag 102. In another particular embodiment, the first side 136 and second side 140 of the bag 102 can define exterior surfaces of the bag 102, interior surfaces of the bag 102, or a combination thereof.

Figure 4:
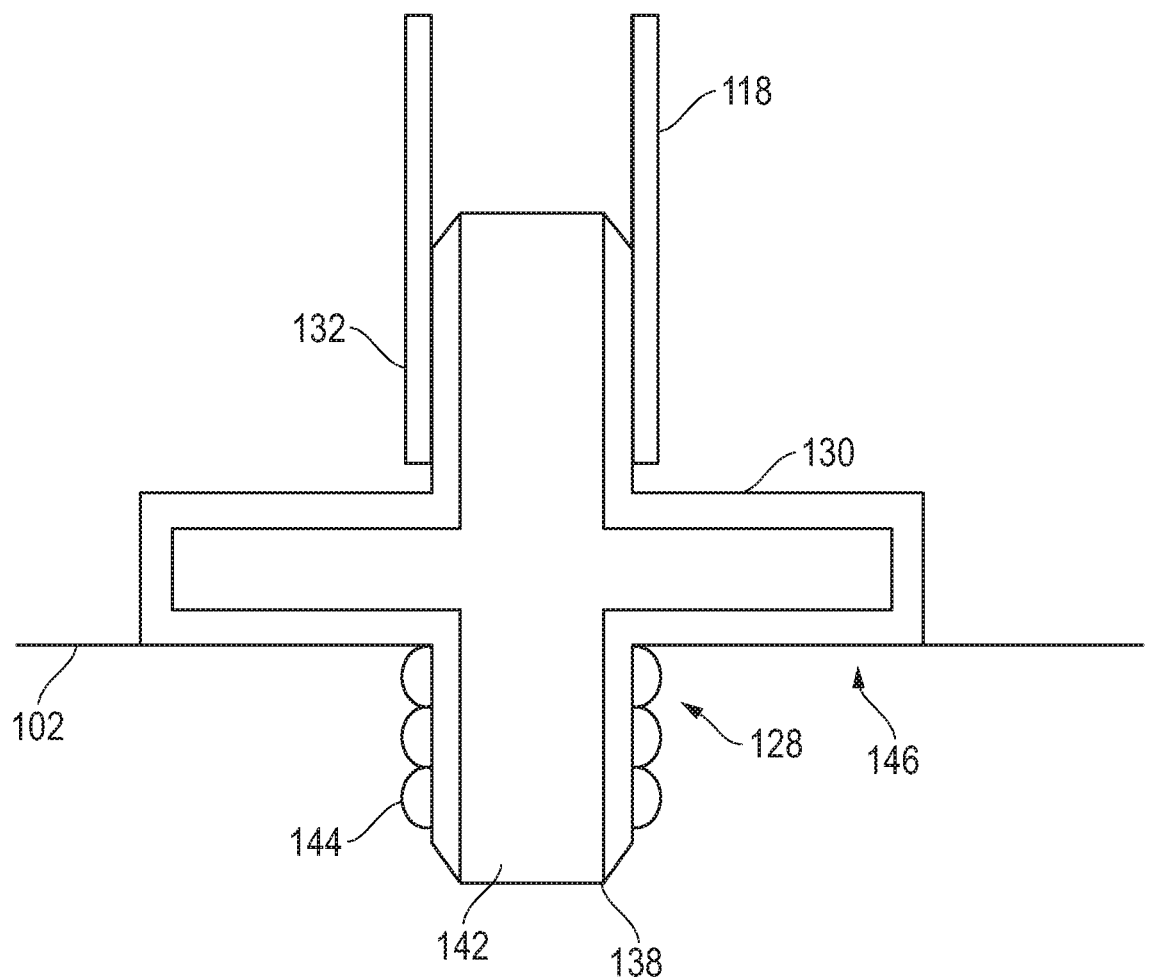
FIG. 4 includes a simplified cross-sectional view of a portion of the system in accordance with an embodiment, as viewed along Line B-B in FIG. 2.

FIG. 4 includes a simplified cross-sectional view of the filter 130 coupled with the bag 102 at the location 128. In an embodiment, the filter 130 is coupled to the bag 102 by an interference fit. In a particular embodiment, the filter 130 can include a barb 144 coupled with the bag 102. As illustrated, the barb 144 can include an undulating or non-straight profile on the second portion 138 such that the second portion 138 engages with the bag 102 at the location 128. The use of a barb may not be necessary where a frictional interference fit is sufficient to maintain engagement between the bag 102 and the filter 130.

The end 132 of the vent 118 can be coupled with the filter 130. In an embodiment, the vent 118 and filter 130 can be coupled together by an interference fit. In another embodiment, the vent 118 and filter 130 can be coupled together by a fastener, such as a threaded fastener. In yet another embodiment, the vent 118 and filter 130 can be welded together. In a further embodiment, the vent 118 and filter 130 can be adhered together by an adhesive or compound.

In an embodiment, the opening 116 is on the first side 136 of the bag 102 (FIG. 3) and an end of the fluid flow path through the vent passageway and lumen 142 is on the second side 140 of the bag 102. In such a manner, fluid flow between the internal volume of the bag 102 and the external environment can pass through the bag 102 at the location 128.

As illustrated in FIG. 4, the filter 130 can include a single-piece body. In another embodiment, the filter 130 can include a multi-piece construction.

In an embodiment, the filter 130 can include a disk shape defining a major surface 146. In an embodiment the major surface 146 of the disk shape can be disposed adjacent a surface of the bag 102. In certain instances, the filter 130 can be inserted into the bag 102 at the location 128 and biased toward the bag 102 until the major surface 146 of the filter 130 contacts the bag 102.

The filter 130 can include a single use filter. In another embodiment, the filter 130 can be reusable. In an embodiment, the filter 130 can include a media or particulate for filtering. In another embodiment, the filter 130 can include a porous structure such as a block or structure of material having perforations or micro-perforations. In a further embodiment, the filter 130 can include a mesh, a screen, or a woven or non-woven medium. In yet another embodiment, the filter can include a combination of filter elements.

In accordance with embodiments described herein, a method of making a system for storing pharmaceuticals or biological media can include coupling the vent 118 to the opening 116 in the flexible sidewall 104 of the bag 102. In a particular embodiment, coupling the vent 118 to the opening 116 is performed by welding. The method can further include installing the filter 130 on the bag 102 at a vertical elevation spaced apart from and above the opening 126. In an embodiment, installing the filter 130 is performed such that the fluid flow through the filter 130 occurs in a direction generally transverse to a major surface of the bag 102. In another embodiment, installing the filter is performed by inserting at least a portion of the filter 130 into the bag, such as for example, at a lumen formed in the bag prior to installing the filter 130. In certain instances, forming the lumen includes forming an opening in the bag 102 with a diameter less than the diameter of the portion of the filter 130 adapted to be received in the lumen. The method can additionally include attaching a free end 132 of the vent 118 to the filter 130. In certain instances, the method can further include bending the vent 118 prior to attaching the free end 132 of the vent 118 to the filter 130.

In accordance with embodiments described herein, a method of using a system for storing pharmaceuticals or biological media can include moving a free end 132 of the vent 118 to the location 128. The method can further include coupling the free end 132 to the bag 102. In an embodiment, the method further includes coupling the filter 130 to the bag 102.

Many different aspects and embodiments are possible. Some of those aspects and embodiments are described below. After reading this specification, skilled artisans will appreciate that those aspects and embodiments are only illustrative and do not limit the scope of the present invention. Embodiments may be in accordance with any one or more of the items as listed below.

Embodiment 1

A system for storing pharmaceuticals or biological media comprising:
  a bag including a flexible sidewall defining an opening; and
  a vent coupled with the flexible sidewall at the opening and defining a vent passageway between an internal volume of the bag and an external environment,
  wherein the vent is coupled with the bag at a location spaced apart from and above the opening.

Embodiment 2

The system of embodiment 1, further comprising a filter coupled with the bag.

Embodiment 3

The system of embodiment 2, wherein the filter is coupled with the bag at the location spaced apart from and above the opening.

Embodiment 4

The system of any one of embodiments 2 and 3, wherein the filter is disposed between the bag and an end of the vent.

Embodiment 5

The system of any one of embodiments 2-4, wherein the filter is coupled with the vent.

Embodiment 6

The system of any one of embodiments 2-5, wherein a portion of the filter is disposed on a first side of the bag and a second portion of the filter is disposed on a second side of the bag.

Embodiment 7

The system of embodiment 6, wherein the first and second sides of the bag both define exterior surfaces of the bag.

Embodiment 8

The system of any one of embodiments 2-7, wherein the filter extends through the bag at the location spaced apart from and above the opening.

Embodiment 9

The system of any one of embodiments 2-8, wherein the filter defines a lumen extending through the bag at the location spaced apart from and above the opening.

Embodiment 10

The system of embodiment 9, wherein the lumen defines a central axis perpendicular with a major surface of the bag when the bag is empty and flattened on its side.

Embodiment 11

The system of any one of embodiments 2-10, wherein the filter is coupled to the bag by an interference fit.

Embodiment 12

The system of any one of embodiments 2-11, wherein the filter comprises a barb coupled with the bag.

Embodiment 13

The system of any one of embodiments 2-12, wherein the vent and filter are coupled together by an interference fit, welded together, held together by a fastener, or a combination thereof.

Embodiment 14

The system of any one of embodiments 2-13, wherein the opening is on a first side of the bag, and wherein an end of a fluid flow path comprising at least a portion of the vent and filter is disposed on a second side of the bag.

Embodiment 15

The system of any one of embodiments 2-14, wherein the filter comprises a disk shape defining at least one major surface adjacent to a surface of the bag.

Embodiment 16

The system of any one of the preceding embodiments, wherein the location spaced apart from and above the opening is disposed at a location adjacent to a handle of the bag.

Embodiment 17

The system of any one of the preceding embodiments, wherein the location spaced apart from and above the opening is disposed in a handle portion of the bag.

Embodiment 18

The system of embodiment 17, wherein the handle portion of the bag is spaced apart from an internal volume of the bag.

Embodiment 19

The system of any one of the preceding embodiments, wherein the vent is welded to the flexible sidewall at a location proximate to the opening.

Embodiment 20

The system of any one of the preceding embodiments, wherein the vent passageway lies along a line having a generally curved profile.

Embodiment 21

The system of any one of the preceding embodiments, wherein the vent further comprises a fluid restrictor adapted to selectively restrict fluid flow through the vent passageway.

Embodiment 22

The system of any one of the preceding embodiments, wherein the vent comprises a flexible material.

Embodiment 23

The system of any one of the preceding embodiments, wherein the bag further comprises a main opening at an upper location of the bag.

Embodiment 24

The system of any one of the preceding embodiments, wherein the bag further comprises at least one fluid port, the fluid port adapted for sampling fluid in the bag, filling the bag, draining the bag, or a combination thereof.

Embodiment 25

The system of any one of the preceding embodiments, wherein the opening is disposed below a fill-line of the bag.

Embodiment 26

The system of embodiment 25, wherein the location spaced apart from and above the opening is disposed above the fill-line of the bag.

Embodiment 27

The system of any one of the preceding embodiments, wherein the bag comprises a collapsible bag.

Embodiment 28

The system of any one of the preceding embodiments, wherein the bag comprises a collapsible bag.

Embodiment 29

A method of making a system for storing pharmaceuticals or biological media comprising:
coupling a vent to an opening in a flexible sidewall of a bag;
installing a filter on the bag at a vertical elevation spaced apart from and above the opening; and
attaching a free end of the vent to the filter.

Embodiment 30

The method of embodiment 29, wherein coupling the vent to the opening is performed by welding.

Embodiment 31

The method of any one of embodiments 29 and 30, wherein installing the filter is performed such that the fluid flow through the filter occurs in a direction generally transverse to a major surface of the bag.

Embodiment 32

The method of any one of embodiments 29-31, further comprising forming a lumen in the bag prior to installing the filter.

Embodiment 33

The method of embodiment 31, wherein installing the filter is performed by inserting at least a portion of the filter into the lumen.

Embodiment 34

The method of any one of embodiments 32 and 33, wherein the filter comprises a barb adapted to form an interference fit with the lumen upon installing the filter in the bag.

Embodiment 35

The method of any one of embodiments 32-34, wherein forming the lumen comprises forming an opening having a diameter less than the diameter of a portion of the filter adapted to be received in the lumen.

Embodiment 36

The method of any one of embodiments 32-35, further including bending the vent prior to attaching the free end of the vent to the filter.

Embodiment 37

The method of any one of embodiments 29-36, wherein attaching the free end of the vent to the filter creates an approximately 180 degree bend in the vent.

Embodiment 38

A method of making a system for storing pharmaceuticals or biological media comprising:
moving a free end of a vent extending from a flexible sidewall of a bag to a location above a non-free end of the vent; and
coupling the free end of the vent to the bag.

Embodiment 39

The method of embodiment 38, further comprising coupling a filter to the bag.

Embodiment 40

The method of embodiment 39, wherein coupling the filter to the bag comprises coupling a barb portion of the filter with an opening in the bag.

Embodiment 41

The method of embodiment 39, wherein coupling the filter to the bag is performed such that the barb passes from a first side of the bag to a second side of the bag.

Embodiment 42

The method of embodiment 39, wherein the opening defines a relaxed diameter less than an outer diameter of the barb.

Embodiment 43

The method of embodiment 39, wherein coupling the free end of the vent to the bag is performed by coupling the free end of the vent to the filter.

Embodiment 44

The method of embodiment 39, wherein coupling the filter to the bag is performed prior to coupling the free end of the vent to the bag.

Embodiment 45

The method of embodiment 39, wherein biasing the free end of the vent is performed such that the non-free end of the vent is disposed at a vertical elevation below the free end of the vent.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

The invention claimed is:

1. A system for storing pharmaceuticals or biological media comprising:
    a bag including a flexible sidewall defining an opening; and
    a vent coupled with the flexible sidewall at the opening and defining a vent passageway between an internal volume of the bag and an external environment,
    wherein the vent is coupled with the bag at a location spaced apart from and above the opening, wherein the location is laterally offset from the opening, further comprising a filter directly coupled to the bag between the bag and an end of the vent, wherein the vent further comprises a fluid restrictor adapted to selectively restrict fluid flow through the vent passageway.

2. The system of claim 1, wherein the filter is coupled with the bag at the location spaced apart from and above the opening.

3. The system of claim 1, wherein the filter is disposed between the bag and an end of the vent.

4. The system of claim 1, wherein a portion of the filter is disposed on a first side of the bag and a second portion of the filter is disposed on a second side of the bag.

5. The system of claim 1, wherein the filter extends through the bag at the location spaced apart from and above the opening.

6. The system of claim 1, wherein the filter defines a lumen extending through the bag at the location spaced apart from and above the opening.

7. The system of claim 1, wherein the filter comprises a barb coupled with the bag.

8. The system of claim 1, wherein the vent and filter are coupled together by an interference fit, welded together, held together by a fastener, or a combination thereof.

9. The system of claim 1, wherein the opening is on a first side of the bag, and wherein an end of a fluid flow path comprising at least a portion of the vent and filter is disposed on a second side of the bag.

10. The system of claim 1, wherein the vent is welded to the flexible sidewall at a location proximate to the opening.

11. The system of claim 1, wherein the bag further comprises at least one fluid port, the fluid port adapted for sampling fluid in the bag, filling the bag, draining the bag, or a combination thereof.

12. The system of claim 1, wherein a line between the location and the opening has an X-component and a Y-component, wherein the X-component is at least 1.01 times greater than the Y-component.

13. The system of claim 1, wherein a line between the location and the opening has an X-component and a Y-component, wherein the Y-component is at least 1.01 times greater than the X-component.

14. The system of claim 1, wherein a line between the location and the opening has an X-component and a Y-component, wherein the Y-component of the line, as measured between the opening and the location, is at least 5 mm.

15. The system of claim 1, wherein the location is disposed adjacent to a handle portion of the bag.

16. The system of claim 1, wherein a line between the opening and location is angularly offset from a Y-axis by at least 1°.

* * * * *